United States Patent [19]

Kataoka et al.

[11] Patent Number: 5,275,702

[45] Date of Patent: Jan. 4, 1994

[54] DISTILLATION METHOD OF SEPARATING ORGANIC SOLVENTS

[75] Inventors: Takehiko Kataoka; Haruo Kawasaki, both of Kawasaki; Harutoshi Ohura; Yoshinobu Uchida, both of Yokkaichi; Akihiko Yasaki; Shinichi Kishimoto, both of Kawasaki, all of Japan

[73] Assignee: Ajinomoto Co., Inc., Tokyo, Japan

[21] Appl. No.: 928,298

[22] Filed: Aug. 12, 1992

[30] Foreign Application Priority Data

Aug. 27, 1991 [JP] Japan .................. 3-214968

[51] Int. Cl.$^5$ .................................. B01D 3/36
[52] U.S. Cl. ......................... 203/85; 203/96; 560/41; 562/608; 562/609; 585/807; 585/868
[58] Field of Search ................... 203/96, 85, 16; 562/608, 609; 585/504, 807, 833, 868; 560/41; 426/548

[56] References Cited

U.S. PATENT DOCUMENTS

| | | | |
|---|---|---|---|
| 1,722,532 | 7/1929 | Maude | 203/16 |
| 1,815,802 | 7/1931 | Schleicher et al. | |
| 2,438,300 | 3/1948 | Schniepp | 203/85 |
| 2,913,492 | 11/1959 | van der Voort | 562/608 |
| 3,347,756 | 10/1967 | Snell | 203/85 |
| 3,718,545 | 2/1973 | Horlenko | |
| 3,933,781 | 1/1976 | Bachman et al. | 560/41 |
| 4,680,403 | 7/1987 | Hisamitsu et al. | 426/548 |
| 4,824,994 | 4/1989 | Takashi et al. | 560/41 |

FOREIGN PATENT DOCUMENTS

| | | |
|---|---|---|
| 0227301 | 7/1987 | European Pat. Off. |
| 1543833 | 10/1968 | France |
| 133559 | 1/1979 | German Democratic Rep. ............ 562/608 |
| 53-116314 | 10/1978 | Japan |
| 63-255244 | 10/1988 | Japan |

OTHER PUBLICATIONS

Azeotropic Data-III-Horsley, Advances In Chemistry Series 116, Wash., D.C. 1973, p. 33.

*Primary Examiner*—Wilbur Bascomb, Jr.
*Attorney, Agent, or Firm*—Oblon, Spivak, McClelland, Maier & Neustadt

[57] ABSTRACT

The present invention discloses a method to separate each component from a mixed solution of organic solvents obtained during the production of α-L-aspartyl-L-phenylalanine methyl ester, which is useful as a sweetener, namely, a mixed solution of acetic acid and toluene or a mixed solution of acetic acid, toluene and formic acid, recovering each component with a high recovery ratio with as small number of operations as possible. The method rationalizes the process and is highly valuable in practical use.

When each component is separated and recovered from a mixed solution containing acetic acid and toluene as the main components, acetic acid and toluene are separated by azeotropic distillation using water as an azeotropic solvent, and when each component is separated and recovered from a mixed solution containing acetic acid, toluene and formic acid as the main components, (a) the mixed solution is distilled and formic acid is recovered from the top of the column and a mixed solution of acetic acid and toluene is recovered from the bottom of the column; and (b) the mixed solution obtained from the bottom is distilled by using water as an azeotropic solvent and toluene is recovered from the top of the column and acetic acid is recovered from the bottom of the column.

3 Claims, No Drawings

DISTILLATION METHOD OF SEPARATING ORGANIC SOLVENTS

BACKGROUND OF THE INVENTION

The present invention relates to a method of separating and recovering each component from a mixed solution of organic solvents obtained during the production of α-L-aspartyl-L-phenylalanine methyl ester (hereinafter referred to as "α-APM"), which is useful as a sweetener, namely, a mixed solution of acetic acid and toluene or acetic acid, toluene and formic acid. A mixed solution obtained during the production of α-APM is generally composed of 15 to 45% by weight of acetic acid and 50 to 80% by weight of toluene in the former case, and 15 to 50% by weight of acetic acid, 40 to 80% by weight of toluene and 1 to 15% by weight of formic acid in the latter case. Each component separated and recovered from the mixed solution can be recycled to an α-APM producing process and reused.

Since acetic acid (boiling point: 118° C.) and toluene (boiling point: 111° C.) form an azeotropic mixture (azeotropic point: 104° C.) containing 34.5% by weight of acetic acid, it is theoretically impossible to separate the mixed solution by a single and simple distillation operation and obtain acetic acid containing substantially no toluene and toluene containing substantially no acetic acid, simultaneously.

In a usual separating method, acetic acid in toluene is first extracted with water, an extracting solvent, into the water phase and the obtained mixed solution of water and acetic acid are then separated by distillation. Separation of water and acetic acid by a conventional distillation method requires as many as 80 to 90 plates and a high reflux ratio. Therefore, azeotropic distillation using an azeotropic solvent (hereinafter referred to as "entrainer"), such as butyl acetate, is generally used so as to obtain a mixed solution of water and the entrainer from the top of the column and obtain acetic acid from the bottom of the column.

In the method, two separating operations, namely, extraction and distillation, are carried out sequentially, and each operation requires its own apparatus. Especially, when the concentration of acetic acid in the mixed solution is high, in order to extract almost all part of the acetic acid into water phase, an extraction column having a large number of plates such as 20 to 30 becomes necessary and the whole equipments including the extraction column in addition to the distillation column become excessively large. Since the production of α-APM requires a large number of solvent recovering processes, it is desirable that the number of operations necessary in each process is as small as possible and that the equipment in each operation is as small as possible.

A technique to simultaneously isolate three components in a mixed solution of acetic acid, toluene and formic acid (boiling point: 101° C.) into each component in a single operation has not been known. However, a technique to separate components in a mixed solution of formic acid and acetic acid by azeotropic distillation adding toluene as an entrainer by utilizing the fact that formic acid and toluene mixed in a weight ratio of 50:50 forms a two-liquid-phase azeotropic mixture (azeotropic point: 86° C.) and to recover formic acid from the top of the distillation column and acetic acid from the bottom of the column is known. In this case, since toluene is not contained in the original mixed solution which is the object of the separation, usually all the toluene phase distilled out at the top of the column is refluxed and only an amount of toluene, being dissolved in the formic acid phase discharged out of the distillation system, is supplied to make up for the discharged amount. However, the mixed solution which is obtained during the production of α-APM originally contains toluene. Therefore, when this known technique is applied to separate the mixed solution, containing toluene, the amount of toluene to be supplied to the distillation system must be taken out and recovered from the toluene phase distilled out at the top of the column. Namely, each component of the mixed solution must be separated, by (i) recovering acetic acid from the bottom of the column, (ii) recovering a mixed solution of formic acid and toluene from the top, (iii) making the mixed solution into two liquid phases, (iv) separating the layers of toluene and formic acid, and (v) recovering each component.

However, the concentration of toluene in the mixed solution obtained during the production of α-APM is as high as 5 to 25 times by weight the concentration of formic acid and a mutual solubility of formic acid and toluene is as high as 8% by weight at 25° C., so if the mixed solution is separated by this conventional method, a considerably large part of formic acid dissolves in the recovered toluene phase. Since the recovered toluene is neutralized and washed, formic acid in the recovered toluene phase is wasted in the form of an aqueous diluted solution. Accordingly, the larger the amount of formic acid in the recovered toluene phase is, the larger loss of formic acid becomes and, as a result, the recovery yield of formic acid becomes poor.

For example, when separating a mixed solution of 7% by weight of formic acid, 25% by weight of acetic acid and 68% by weight of toluene by this conventional method, as much as 84% of the formic acid in the mixed solution supplied to the distillation system is taken out dissolving in the recovered toluene phase. Because this part of the acid becomes a waste, the recovery ratio of formic acid becomes as low as 16%. From the point of view of the profitability of the separating and recovering process, the desirable recovery ratio of formic acid is not less than 90%, but that of formic acid obtained by this conventional method falls far below the value.

Consequently, when the recovery of formic acid is taken into consideration, this conventional technique cannot be applied to the process of producing α-APM.

The present inventors have intensively studied to solve the above-described problems and to establish a method of separating and recovering each of the components from a mixed solution of acetic acid and toluene or a mixed solution of acetic acid, toluene and formic acid with high recovery ratios.

As a result of the studies carried out by the present inventors to solve the problems, it has been found that it is possible to separate each of the components from a mixed solution of acetic acid and toluene in a single operation by azeotropic distillation using water as an entrainer with high recovery ratios. Further, it has also been found that it is possible to separate and recover each of the components from a mixed solution of acetic acid, toluene and formic acid only by two distilling operations, namely; (a) distilling the mixed solution and recovering formic acid from the top and a mixture of acetic acid and toluene from the bottom; and (b) distilling the mixture of acetic acid and toluene using water as an azeotropic solvent and recovering toluene from the top and acetic acid from the bottom. Based on the two findings described above, the present inventors have attained the present invention.

SUMMARY OF THE INVENTION

An object of the present invention is to provide a method of separating and recovering each of the main components from a mixed solution containing acetic acid and toluene as the main components, which comprises separating acetic acid and toluene by azeotropic distillation using water as an azeotropic solvent.

Another object of the present invention is to provide a method of separating and recovering each of the main components from a mixed solution containing acetic acid, toluene and formic acid as the main components, which process comprises steps of; (a) distilling the mixed solution and recovering formic acid from the top of the distillation column and recovering a mixed solution of acetic acid and toluene from the bottom of the column; and (b) distilling the mixed solution of acetic acid and toluene using water as an azeotropic solvent and recovering toluene from the top and acetic acid from the bottom of the distillation column.

One more object of the present invention is to provide a method of separating and recovering each main component from a mixed solution containing acetic acid and toluene or a mixed solution containing acetic acid, toluene and formic acid as the main components with simple operations and high recovery ratios.

Further object of the present invention is to provide a method of separating and recovering each main component from a mixed solution containing acetic acid and toluene or a mixed solution containing acetic acid, toluene and formic acid as the main components and being obtained during the production of α-APM.

DETAILED DESCRIPTION OF THE INVENTION

The present invention relates to a method of separating and recovering each component from a mixed solution of organic solvents obtained during the production of α-L-aspartyl-L-phenylalanine methyl ester, which is useful as a sweetener, namely, a mixed solution containing acetic acid and toluene or acetic acid, toluene and formic acid. A mixed solution obtained during the production of α-APM is generally composed of 15 to 45% by weight of acetic acid and 50 to 80% by weight of toluene in the former case, and 15 to 50% by weight of acetic acid, 40 to 80% by weight of toluene and 1 to 15% by weight of formic acid in the latter case. Each component separated and recovered from the mixed solution can be recycled to an α-APM producing process and reused.

Water and toluene form a two-liquid-phase azeotropic mixture (azeotropic point: 84° C.) in a weight ratio of 20:80, so if the mixed solution of acetic acid and toluene is distilled in the presence of water, it is possible to obtain a mixture of water and toluene from the top of the distillation column and acetic acid from the bottom of the column. As the mutual solubility of water and toluene is as low as 0.1% by weight at ordinary temperature, it is possible to separate the distillate obtained from the top into a water phase and a toluene phase and recover water and toluene separately or reflux them into the column separately. When it comes to separating and recovering a mixed solution containing acetic acid, toluene and formic acid into each component, an entire or a most part of the toluene phase distilled out at the top of the distillation column is refluxed into the column without recovering it, in order to obtain a mixed solution of toluene and acetic acid from the bottom of the column, and the mixed solution is azeotropically distilled using water as an entrainer, in the same manner as described above. In this case, a recovery ratio of formic acid from the top is not less than 98%.

In other words, the present invention relates to a method of separating and recovering each of the main components from a mixed solution containing acetic acid and toluene as the main components by azeotropic distillation using water as an azeotropic solvent (hereinafter referred to as "first method"), and further relates to a method of separating and recovering each of the main components from a mixed solution containing acetic acid, toluene and formic acid as the main components, which method comprises the steps of: (a) distilling the mixed solution and recovering formic acid from the top of the distillation column and recovering a mixed solution of acetic acid and toluene from the bottom of the column; and (b) distilling the mixed solution recovered from the bottom by using water as an azeotropic solvent and recovering toluene from the top of the distillation column and recovering acetic acid from the bottom of the column (hereinafter referred to as "second method").

The first method of the present invention comprises one distilling operation and the second method comprises two distilling operations and the column being used in the both methods can be a packed or a plate column. The composition of a mixed solution which is obtained during the production of α-APM is 15 to 45% by weight of acetic acid and 50 to 80% by weight of toluene in the first method and 15 to 50% by weight of acetic acid, 40 to 80% by weight of toluene and 1 to 15% by weight of formic acid in the second method, however, the composition of the mixed solution as the object of the present invention is not restricted to the range described above, namely, the method of the present invention is applicable to the separation of a mixed solution containing acetic acid and toluene or a mixed solution containing acetic acid, toluene and formic acid in a broader range than exemplified above. The mixed solution to be separated in the both methods may contain components other than the main components as long as these minor components do not cause any problem in the quality of the recovered solvents to be reused.

The water which is used as the entrainer in the distilling operation of the first method and in the second distilling operation of the second method (both distilling operations are hereinafter referred to as "acetic acid separating operation") can be supplied combined with or separately from the mixed solution. Since the distillate obtained from the top of the column in either of these two distilling operations constitutes two liquid phases of toluene and water, it is preferable to reduce an amount of water supplied from the outside of the system by refluxing the water phase of the distillate after separating from the toluene phase. If necessary, the toluene phase can also be refluxed with water, with the reflux ratio that varies according to the situation.

In the first distilling operation of the second method (hereinafter referred to as "formic acid separating operation"), it is preferable to reflux the entire part of the toluene phase distilled out at the top of the distillation column, but according to the situation, it can be more preferable to take out a part of the toluene phase from the system. Further, it is sometimes preferable to reflux a part of the formic acid phase with the reflux ratio that varies according to the situation.

Several percentages of acetic acid and toluene dissolve in the recovered formic acid in the present invention. But because acetic acid and toluene in the recovered formic acid can be reused at the time of recycling it, these facts do not mean any loss of the solvents. Although the concentration of formic acid in the recovered formic acid phase does not exceed 92% by weight, there is no problem in reusing it so long as the concentration of the acid is not less than 65% by weight. Accordingly, with this operation, it is possible to recover formic acid having a purity which causes no problem in reusing it, and also is possible to obtain a mixed solution of acetic acid and toluene containing not more than 0.1% by weight of formic acid, as the bottom liquid.

In the present invention, the term, "bottom liquid" means the liquid obtained at the bottom of the distillation column.

An amount of heat applied to the bottom of the column in each operation varies with the conditions such as the composition of the feed, the composition of the bottom liquid and the number of plates in the recovering part of the column. If the heat applied during the formic acid separating operation is too much, a large amount of acetic acid distills out at the top of the column, which causes the problem that purity of the recovered formic acid becomes low and that a phase separation of the distillate becomes difficult. For example, when the temperature of the distillate is 45° C., and the concentration of acetic acid therein is not less than 18% by weight, the distillate does not constitute a two-phase liquid but a uniform solution. If an amount of heat applied during the acetic acid separating operation is too small, a considerable amount of toluene and water remains in the bottom liquid. On the other hand, if the amount is too large, a considerable amount of acetic acid distills out at the top. Therefore, it is necessary to determine the amount of heat applied to the bottom of the columns with extreme care.

The composition profile and the temperature profile in the column in each of the operations can be controlled by changing the amount of liquid to be refluxed at the top and/or the amount of heat applied to the bottom. From the viewpoints of the stability and the convenience of the control, it is preferable to measure the temperature at a certain point in the column and control the amount of each phase to be refluxed so that the temperature at the point becomes constant. In this case, it is necessary to select a point at which the boiling point varies much with the change in the composition, as the temperature measuring point.

With the present invention, it is possible to recover each component from a mixed solution of acetic acid and toluene or a mixed solution of acetic acid, toluene and formic acid which is obtained during the production of α-APM by one or two distilling operations. Since a number of operations required for the separation is reduced, the scale of the equipment and the number of workers required can also be reduced, which leads to the rationalization of the process. Thus, the present invention is valuable in practical use.

The present invention will now be explained in more detail with reference to the following example.

EXAMPLE

A continuous distilling experiment with a mixed solution of acetic acid, toluene and formic acid as a feed was carried out using a packed distillation column that was 50 mm in diameter and 5 m in packed height under ordinary pressure. As packings, 5 mm, Raschig rings made of porcelain, were used.

A mixed solution of acetic acid and toluene (a concentration of acetic acid: 27.0% by weight) was first charged into the bottom of the column and the column was heated. Just before the vapor of the solution rising to the top of the column was condensed by a total condenser and flowed into a decanter, supply of formic acid, which had been stocked in the decanter in advance, to the top was started using a refluxing pump.

When the temperature at the intermediate point between the feeding point (2 m above the bottom) and the top reached 90° C., the operation at total reflux was started. When the temperatures measured at an interface in the decanter and at four points in the column became constant, supply of the feed having the composition shown in Table 1, to the top was started at a rate of 250 g per hour.

Thereafter, an amount of the liquid to be refluxed and an amount of heat applied to the bottom were controlled to stabilize the level of the interface in the decanter and the temperatures measured at the four points in the column. Finally, the total amount of the toluene phase and a part of the formic acid phase were refluxed and the remaining part of the acid was taken out of the system. The reflux ratio was settled at 12.0 (mol/mol). Temperatures at the top and at the bottom were 86° C. and 107° C., respectively, under the steady operation.

After 5 hours of the steady distilling operation, the flow rates of the bottom liquid and the distillate (formic acid phase) were measured and the compositions thereof were analyzed. The results are shown in Table 1. Thereafter, the distillation was carried out for further 10 hours in a stationary state and finally 200 g of the distillate (formic acid phase) and 2,300 g of the bottom liquid were obtained. The recovery ratio of formic acid was 99%.

TABLE 1

| Flow Rate (g/hr) | | Feed 250 | Bottom Liquid 230 | Distillate 19 |
|---|---|---|---|---|
| Composition (% by weight) | Acetic acid | 25.2 | 27.0 | 4.6 |
| | Toluene | 68.0 | 73.0 | 7.7 |
| | Formic acid | 6.8 | trace | 87.6 |

Then a continuous distillation experiment was carried out using the same distillation column and the same packings and supplying, as the feed, a mixed solution of acetic acid and toluene, which had been obtained as the bottom liquid in the above-described experiment.

Acetic acid was first charged into the bottom of the column and heating was started. Supply of the feed having the composition shown in Table 2, was started at a rate of 200 g per hour when the vapor of acetic acid rose to the intermediate point between the feeding point and the top of the column.

Just before the vapor rising to the top was condensed by the total condenser and flowed into the decanter, supply of water, which had been stocked in the decanter in advance, to the top was started using a refluxing pump.

Thereafter, an amount of the liquid to be refluxed and an amount of the heat applied to the bottom were controlled to stabilize the level of the interface in the decanter and the temperatures measured at the four points in the column. Finally, the total amount of the water phase and a part of the toluene phase were refluxed and the remaining part of the toluene was taken out of the system. The reflux ratio was settled at 4.2 (mol/mol). Temperatures at the top and at the bottom were 84° C. and 118° C., respectively, under the steady operation.

After 5 hours of steady distilling operation, the flow rates of the bottom liquid and the distillate (toluene phase) were measured and the compositions thereof were analyzed. The results are shown in Table 2.

TABLE 2

| Flow Rate (g/hr) | | Feed 200 | Bottom Liquid 54 | Distillate 147 |
|---|---|---|---|---|
| Composition (% by weight) | Acetic acid | 26.8 | 99.9 | 0.1 |
| | Toluene | 73.2 | trace | 99.8 |
| | Water | — | trace | trace |

What is claimed is:

1. A method of separating and recovering each of the main components from a mixed solution containing acetic acid, toluene and formic acid as the main components, which method comprises steps of:
    (a) distilling said mixed solution and recovering formic acid from the top of a distillation column and recovering a mixed solution of acetic acid and toluene from the bottom of the column; and
    (b) distilling the solution of acetic acid and toluene recovered from the bottom using water as an azeotropic solvent and recovering toluene from the top and acetic acid from the bottom of the distillation column.

2. The method according to claim 1, wherein the concentrations of acetic acid, toluene and formic acid in said mixed solution are 15 to 50% by weight, 40 to 80% by weight and 1 to 15% by weight, respectively.

3. The method according to claim 1, wherein said mixed solution is a mixed solution of organic solvents obtained during production of α-L-aspartyl-L-phenylalanine methyl ester.

* * * * *